US009598380B2

(12) United States Patent
Bottaro et al.

(10) Patent No.: US 9,598,380 B2
(45) Date of Patent: Mar. 21, 2017

(54) FACILE METHOD FOR PREPARATION OF 5-NITROTETRAZOLATES USING A BATCH SYSTEM

(71) Applicants: SRI International, Menlo Park, CA (US); Pacific Scientific Energetic Materials Company, Chandler, AZ (US)

(72) Inventors: Jeffrey C. Bottaro, Menlo Park, CA (US); Mark A. Petrie, Menlo Park, CA (US); Jon G. Bragg, Phoenix, AZ (US); John W. Fronabarger, Sun Lakes, AZ (US); Michael D. Williams, Gilbert, AZ (US)

(73) Assignees: SRI International, Menlo Park, CA (US); Pacific Scientific Energetic Materials Company, LLC, Chandler, AZ (US)

( * ) Notice: Subject to any disclaimer, the term of this patent is extended or adjusted under 35 U.S.C. 154(b) by 0 days.

(21) Appl. No.: 14/731,613

(22) Filed: Jun. 5, 2015

(65) Prior Publication Data
US 2015/0361057 A1  Dec. 17, 2015

Related U.S. Application Data

(60) Provisional application No. 62/011,207, filed on Jun. 12, 2014.

(51) Int. Cl.
C07D 257/06 (2006.01)
(52) U.S. Cl.
CPC ................ C07D 257/06 (2013.01)
(58) Field of Classification Search
None
See application file for complete search history.

(56) References Cited

U.S. PATENT DOCUMENTS

| | | |
|---|---|---|
| 2,066,954 A | 1/1937 | von Herz |
| 3,054,800 A | 9/1962 | Burchfield et al. |
| 3,111,524 A | 11/1963 | Wiley et al. |
| 4,093,623 A | 6/1978 | Gilligan et al. |
| 4,094,879 A | 6/1978 | Bates et al. |
| 4,552,598 A | 11/1985 | Lee et al. |
| 6,375,871 B1 | 4/2002 | Bentsen et al. |
| 6,437,104 B1 | 8/2002 | Nickel et al. |
| 6,469,147 B2 | 10/2002 | Nickel et al. |
| 6,495,016 B1 | 12/2002 | Nawracala |
| 6,648,015 B1 | 11/2003 | Chow et al. |
| 6,737,026 B1 | 5/2004 | Bergh et al. |
| 7,253,288 B2 | 8/2007 | Renz et al. |
| 2007/0161801 A1 | 7/2007 | Renz et al. |

FOREIGN PATENT DOCUMENTS

| | | |
|---|---|---|
| WO | 0159013 | 8/2001 |
| WO | 03037502 | 5/2003 |
| WO | 2006029193 | 3/2006 |
| WO | 2014116654 | 7/2014 |

OTHER PUBLICATIONS

Klapoetke et al., Z. Anorg. Allg. Chem., 2013, 639, (5), 681-688 (Published Online: Mar. 15, 2013).*
Klapotke et al., Inorg. Chem. 2008, 47, 6014-6027.*
International Patent Application No. PCT/US2014/012472, International Preliminary Report on Patentability dated Aug. 6, 2015.
Fortt et al., Continuous-Flow Generation of Anhydrous Diazonium Species, Organic Process Research & Development, 2003, 762-768, vol. 7, No. 5.
Wootton et al., On-Chip Generation and Reaction of Unstable Intermediates, Lab-On-A-Chip, 2002, 4, 5-7.
Doyle et al., Alkyl Nitrite-Metal Halide Deamination Reaction. 2. Substitutive Deamination of Arylamines by Alkyl Nitrites and Cooper (II) Halides. A Direct and Remarkably Efficient Conversion of Arylamines to Aryl Halides, J. Org. Chem., 1977, 2426-2431, vol. 42, No. 14.
Tegrothenhuis et al., Normal gravity testing of a microchannel phase separator for resource utilization, NASA/CR-2001-210955 (Jun. 2001).
Brooks et al., Component development for a microchannel in situ propellant production system, 2002, AIChE 2002 Spring National Meeting held Mar. 10-14, 2002 in New Orleans, Louisiana.
Ahn et al., Centrifugal gas-liquid separation under low-gravity conditions, Separation and Purification Technology, 2000, 121-129, vol. 19, No. 1.
Gunther et al., Transport and reaction in microscale segmented gas-liquid flow, Lab-On-A-Chip, 2004, 4, 278-286.
Amon et al., Direct Methanol Micro Fuel Cell for Powering Micro Sensors, http://www.darpa.mil/mto/mpg/summaries/2003.sub.--1/cmu.html (2003).
Kralj et al., Preparation of Sodium Nitrotetrazolate Using Microreactor Technology, American Institute of Aeronautics and Astronautics, 41.sup.st AIAA/ASME/SAE/ASEE Joint Propulsion Conference and Exhibit, Jul. 10-13, 2005, Tuscan, AZ.
C. Galli, "Substituent Effects on the Sandmeyer reaction. Quantitative Evidence for Rate-determining Electron Transfer" J. Chem. Soc. Perkin Trans. II, 1984, pp. 897-902.
Lowe, et al. 'Flow chemistry: Imidazole-based ionic liquid syntheses in micro-scale', Chemical Engineering Journal, 2010, vol. 163, No. 3, pp. 429-437.
PCT/US2014/012472, International Search Report and Written Opinion dated May 2, 2014, 10 pages.
U.S. Appl. No. 14/160,998, Final Office Action dated Oct. 22, 2015.

(Continued)

Primary Examiner — Alicia L Otton
(74) Attorney, Agent, or Firm — Kilpatrick Townsend & Stockton LLP

(57) ABSTRACT

Described are methods for preparing salts of 5-nitrotetrazolate by reacting 5-aminotetrazole, an acid, and sodium nitrite in water in a batch reaction at an elevated temperature. As examples, the acid is nitric acid, sulfuric acid, perchloric acid, or hydrochloric acid, and the elevated temperature is at or above 65° C.

15 Claims, 1 Drawing Sheet

(56) References Cited

OTHER PUBLICATIONS

International Patent Application No. PCT/US2016/013858, Search Report and Written Opinion dated Apr. 6, 2016.
U.S. Appl. No. 14/160,998, Non-Final Office Action dated May 27, 2016.
Gutmann et al., Synthesis of 5-Substituted 1 H-Tetrazoles from Nitriles and Hydrazoic Acid by Using a Safe and Scalable High-Temperature Microreactor Approach, Angewandte Chemie International Edition, vol. 49, 2010, pp. 7101-7105.

* cited by examiner

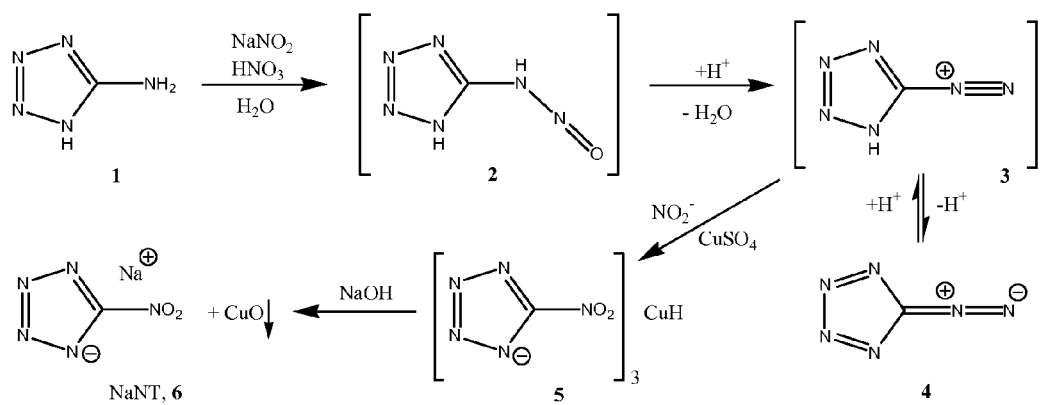

FACILE METHOD FOR PREPARATION OF 5-NITROTETRAZOLATES USING A BATCH SYSTEM

CROSS REFERENCE TO RELATED APPLICATIONS

This application is related to and claims priority benefits from U.S. Provisional Application Ser. No. 62/011,207 ("the '207 application"), filed on Jun. 12, 2014, entitled FACILE METHOD FOR PREPARATION OF 5-NITROTETRAZOLATES. The '207 application is hereby incorporated in its entirety by this reference.

FIELD OF THE INVENTION

This invention relates to explosives, and in particular to a method for preparation of salts of 5-nitrotetrazolate, a reactant used in preparation of a variety of energetic materials.

BACKGROUND

Sodium 5-nitrotetrazolate ("NaNT," 6) has found application as both a stand-alone energetic material and as a reactant or constituent in a variety of explosives and propellants. Typically, NaNT is synthesized via a Sandmeyer type reaction that involves displacement of a diazonium group by a nucleophile, in this case nitrite ion resulting in a nitro group, in the presence of cupric salts. C. Galli, "Substituent Effects on the Sandmeyer reaction. Quantitative Evidence for Rate-determining Electron Transfer" *J. Chem. Soc. Perkin Trans. II*, No. 5, 1984, pp. 897-902; U.S. Pat. No. 4,093,623. Energetics chemists have been utilizing this method for a number of years to produce NaNT in small batches.

This procedure, outlined in FIG. 1, involves addition of a solution of commercially available 5-aminotetrazole ("5-AT," 1) in aqueous nitric acid to a solution of copper(II) sulfate and sodium nitrite to generate the diazonium ion (3), which undergoes substitution to afford the acid copper salt of 5-nitrotetrazole ("5-NT," 5). During the addition of the 5-AT and nitric acid, the reaction temperature is normally tightly controlled at or below 18° C. due to the thermal instability of the diazonium intermediate. The second process step utilizes aqueous sodium hydroxide to convert the acid copper salt of 5-NT into NaNT and generates copper oxide as a byproduct.

This method is problematic, particularly during large scale procedures, due to "micro-detonations" which occur if the mixing of the 5-AT and sodium nitrite solutions is not tightly controlled. These micro-detonations may be caused by nitrogen oxide fumes from the reaction solution reacting with droplets of 5-AT on surfaces in the reactor to form 5-diazotetrazole (4), which may spontaneously detonate in solution when the concentration exceeds 1%.

Aside from being psychologically disturbing for operators, these micro-detonations may be strong enough to break glass and may result in release of the potentially explosive reaction mixture. It was determined that inclusion of a small amount of $CuSO_4$ to the 5-AT solution prior to addition to the $CuSO_4$-nitrite solution was effective in preventing the micro-detonations by catalyzing conversion of 5-diazotetrazole, in the presence of nitrite, to 5-NT. Use of these cupric salts however, add additional steps (and cost and/or time) to the procedure, which result in lower overall reaction yields. These additional operations include two manual filtration steps in which operators are exposed to considerable quantities of $CuH(5-NT)_3$ and NaNT, both of which are explosives. In considering this process, it is quite clear that a less hazardous, alternate procedure is needed for large scale laboratory production of NaNT.

U.S. Pat. No. 7,253,288 to R. N. Renz, M. D. Williams, and J. W. Fronabarger, also describes an alternate method for producing NaNT utilizing microreactor technology, which does not require the use of copper to stabilize the tetrazole diazonium intermediate and involves direct reaction of 5-AT/nitric acid with sodium nitrite at ambient temperature and in a continuous flow regime. Unlike a batch process, this procedure generates only very small amounts of the unstable reaction intermediates in a dilute media and they are subsequently consumed via substitution as a part of the flow process. This process provides a safe method for preparation of 5-nitrotetrazolates as only minor amounts of the intermediates are generated per unit time and accumulation is not possible, but requires extensive time and an appropriate microreactor system optimized for 5-NT production.

The methods for preparation of 5-nitrotetrazolate salts outlined above may be prohibitive either in terms of time and safety for the batch process or for possessing an appropriate microreactor system optimized for 5-NT production for the flow process.

There is a need to improve the efficiency and safety of the chemical process by providing a method for preparation of 5-nitrotetrazolate salts, specifically NaNT, quickly from 5-AT and utilizing a method in which all of the unstable intermediates are immediately and fully consumed.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments, a method of preparing salts of 5-nitrotetrazolate comprises reacting 5-aminotetrazole, an acid, and sodium nitrite in water in a batch reaction at an elevated temperature.

The acid may be nitric acid, sulfuric acid, perchloric acid, or hydrochloric acid. The method may further comprise reacting about 2.1 moles of sodium nitrite and about 1.1 mole of nitric acid per mole of 5-aminotetrazole.

In some embodiments, the method comprises reacting about 2 moles to about 5 moles of sodium nitrite per mole of 5-aminotetrazole. The method may further comprise reacting at least 1 mole to about 1.2 moles of the acid per mole of 5-aminotetrazole.

In certain embodiments, the elevated temperature is at or above 65° C.

According to certain embodiments of the present invention, a reaction product of (a) 5-aminotetrazole, (b) a nitrite salt, (c) an acid, and (d) water, is prepared via a batch reaction at an elevated temperature.

In some embodiments, about 2 moles to about 5 moles of the nitrite salt are supplied to the batch reaction per mole of 5-aminotetrazole. In further embodiments, at least 1 mole to about 1.2 moles of the acid are supplied to the batch reaction per mole of 5-aminotetrazole.

In some embodiments, the nitrite salt is sodium nitrite or potassium nitrite. In these embodiments, the acid is nitric acid, sulfuric acid, perchloric acid, or hydrochloric acid. In these embodiments, about 2.1 moles of sodium nitrite and about 1.1 mole of nitric acid may be supplied to the batch reaction per mole of 5-aminotetrazole.

In certain embodiments, the elevated temperature is at or above 65° C.

According to certain embodiments of the present invention, a method for preparing a salt of 5-nitrotetrazolate comprises the steps of (a) providing an aqueous solution of 5-aminotetrazole and an acid (solution A), (b) providing an aqueous solution of a nitrite salt (solution B), (c) heating both solutions to an elevated temperature, (d) adding solution A to solution B dropwise with rapid stirring and a slow addition rate, and (e) cooling the mixture.

In some embodiments, the method comprises reacting about 2 moles to about 5 moles of the nitrite salt per mole of 5-aminotetrazole. The method may further comprise reacting at least 1 mole to about 1.2 moles of the acid per mole of 5-aminotetrazole.

In some embodiments, the nitrite salt is sodium nitrite or potassium nitrite. In these embodiments, the acid is nitric acid, sulfuric acid, perchloric acid, or hydrochloric acid. The method may further comprise reacting about 2.1 moles of sodium nitrite and about 1.1 mole of nitric acid per mole of 5-aminotetrazole.

In certain embodiments, the elevated temperature is at or above 65° C.

In some embodiments, the slow addition rate is a duration that is greater than about 5 minutes.

According to certain embodiments of the present invention, a method for preparing sodium 5-nitrotetrazolate comprises the steps of (a) providing an aqueous solution of 5-aminotetrazole and nitric acid (Solution A), (b) providing an aqueous solution of sodium nitrite (solution B), (c) heating both solutions to an elevated temperature; (d) adding solution A to solution B dropwise with rapid stirring and a slow addition rate; and (e) cooling the mixture.

In some embodiments, the method comprises providing about 2.1 moles of sodium nitrite and about 1.1 mole of nitric acid per mole of 5-aminotetrazole.

In certain embodiments, the elevated temperature is at or above 65° C.

In some embodiments, the slow addition rate is a duration that is greater than about 5 minutes.

BRIEF DESCRIPTION OF THE DRAWINGS

FIG. 1 is a depiction of a method used for preparation of NaNT, according to certain embodiments of the present invention.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

According to certain embodiments, a procedure has been developed which provides facile access to high purity NaNT by combining the reactants at an elevated temperature. Under appropriate conditions, the diazonium formation and substitution occur at such a rapid rate that there is no opportunity for buildup of hazardous intermediates.

An advantage of the present method is that copper(II) is not required for intermediate stabilization and so there is no need for isolation or separation of byproducts. In addition, the process provides a high purity, concentrated aqueous solution of NaNT which may be directly utilized in subsequent reactions or cooled to induce crystallization and isolated as an end product.

This invention provides a simple, single reactor process for the synthesis of 5-nitrotetrazolates starting from 5-aminotetrazole and which converts it, via a Sandmeyer reaction, to a salt of 5-nitrotetrazolate.

According to certain embodiments of the present invention, NaNT may be prepared by reacting 5-AT, a suitable acid such as nitric, sulfuric or perchloric acid, and sodium nitrite in water in a batch reaction at temperatures at or above 65° C. The components may be reacted under conditions suitable to synthesize NaNT.

In certain embodiments, the components may be reacted by mixing 5-AT and an appropriate acid in water, heating the mixture, and then adding the warm mixture dropwise to a heated solution of sodium nitrite in water. The mixture may be maintained in an elevated temperature range of about 50° C. to about 90° C., further in an elevated temperature range at or above 65° C., and still further at an elevated temperature of about 65° C.

As an example, 5-AT and nitric acid may be combined in minimum water. In certain embodiments, the mixture is heated to an elevated temperature at or above 65° C. to afford a clear solution which may be added dropwise to a solution of sodium nitrite, also held at or above 65° C. In some cases, the mixture displays extreme effervescence during the slow dropwise addition. After the addition is complete, the resulting light yellow solution may be cooled to room temperature. The resulting NaNT may be isolated or used as is. The process provides a 90-95% yield of NaNT.

The duration of the addition step may be a duration that is greater than about 5 minutes, alternatively greater than about 40 minutes, alternatively, about 30 minutes. Slow addition is preferred to prevent the formation of undesirable by-products.

It will be understood that a salt of 5-nitrotetrazolate may be prepared by reacting any suitable nitrite salt. Suitable nitrite salts may include, but are not limited to, sodium or potassium. Likewise any suitable acid may be employed. Suitable acids include, but are not limited to, perchloric acid, sulfuric acid, nitric acid or hydrochloric acid. Likewise, any suitable solvent or combination of solvents may be used. Suitable solvents include, but are not limited to, water.

The nitrite salt may be supplied in a molar ratio of at least 2 moles to about 5 moles per mole of 5-AT. A suitable acid may be supplied in a molar ratio of at least 1 mole to about 1.2 moles per mole of 5-AT (the second proton required for diazotization presumably comes from the 5-AT). For example, sodium nitrite may be supplied in a molar ratio of about 2.1 moles per mole of 5-AT, while nitric acid may be supplied in a molar ratio of about 1.1 mole per mole of 5-AT.

A solvent may be supplied in an amount that is suitable to effectuate the reaction between 5-AT, a nitrite salt, and a suitable acid. As a more specific example, water (or other solvent) may be supplied in an amount that is suitable to effectuate the reaction between 5-AT, a nitrite salt, and a suitable acid.

The product contemplated and made by the methods of the present application (in at least some aspects of the present subject matter, NaNT) may be found suitable for use as explosives and, in particular, as an intermediate for primary explosives. Thus, the present application also contemplates methods for preparing compounds suitable for use as primary explosives, and devices employing such compounds as additives. Benefits include quick, simple and safe preparation with very low toxicity waste streams for both military and commercial applications.

EXAMPLES

The following examples demonstrate the preparation and characterization of a material as taught herein.

Example 1

5-AT (1.0 g, 11.76 mmol) and nitric acid (0.72 mL of 16.4 mmol/mL, 1.1 eq.) were combined in a small beaker with 5 mL water (solution A). A 20 mL beaker was charged with sodium nitrite (1.78 g, 2.2 eq.) and 10 mL of water (solution B). Both solutions were heated to 65° C. Solution A was added dropwise to solution B while solution B was rapidly stirred at 65° C. Extensive effervescence occurred on addition of each drop of solution A and addition was suspended temporarily while the effervescence subsided. The rate of addition was such that the addition of the entire solution A to solution B occurred in 30 minutes. During the addition, the solution went from clear to light yellow in color and was free of solids. After the addition was complete, the mixture was allowed to cool to ambient temperature. Analysis (HPLC or FTIR) of the reaction mixture indicated sodium 5-nitrotetrazolate with >90% yield.

Example 2

5-AT (1.0 g, 11.76 mmol) and perchloric acid (1.11 mL of 11.70 mmol/mL, 1.1 eq.) were combined in a small beaker with 5 mL water (solution A). A 20 mL beaker was charged with sodium nitrite (1.78 g, 2.2 eq.) and 10 mL of water (solution B). Both solutions were heated to 65° C. Solution A was added dropwise to solution B while solution B was rapidly stirred at 65° C. Extensive effervescence occurred on addition of each drop of solution A and addition was suspended temporarily while the effervescence subsided. The rate of addition was such that the addition of the entire solution A to solution B occurred in 30 minutes. During the addition the solution went from clear to light yellow in color and was free of solids. After the addition was complete, the mixture was allowed to cool to ambient temperature. Analysis (HPLC or FTIR) of the reaction mixture indicated sodium 5-nitrotetrazolate with >90% yield.

Example 3

5-AT (1.0 g, 11.76 mmol) and sulfuric acid (0.65 mL of 17.60 mmol/mL, 1.0 eq.) were combined in a small beaker with 5 mL water (solution A). A 20 mL beaker was charged with sodium nitrite (2.84 g, 3.5 eq.) and 10 mL of water (solution B). Both solutions were heated to 65° C. Solution A was added dropwise to solution B while solution B was rapidly stirred at 65° C. Extensive effervescence occurred on addition of each drop of solution A and addition was suspended temporarily while the effervescence subsided. The rate of addition was such that the addition of the entire solution A to solution B occurred in 30 minutes. During the addition the solution went from clear to light yellow in color and was free of solids. After the addition was complete, the mixture was allowed to cool to ambient temperature. Analysis (HPLC or FTIR) of the reaction mixture indicated sodium 5-nitrotetrazolate with >90% yield. Note: Utilizing sulfuric acid, additional nitrite salt is required during the reaction due to generation of nitrosylsulfuric acid, part of which may be lost as NOx.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of preparing sodium salts of 5-nitrotetrazolate comprising reacting 5-aminotetrazole, an acid, and sodium nitrite in water in a batch reaction at an elevated temperature at or above 65° C.

2. The method of claim 1, wherein the acid is nitric acid, sulfuric acid, perchloric acid, or hydrochloric acid.

3. The method of claim 2, wherein the method comprises reacting about 2.1 moles of sodium nitrite and about 1.1 mole of nitric acid per mole of 5-aminotetrazole.

4. The method of claim 1, wherein the method comprises reacting about 2 moles to about 5 moles of sodium nitrite per mole of 5-aminotetrazole.

5. The method of claim 4, wherein the method comprises reacting at least 1 mole to about 1.2 moles of the acid per mole of 5-aminotetrazole.

6. A method for preparing a sodium salt of 5-nitrotetrazolate, comprising the steps of:
    (a) providing an aqueous solution of 5-aminotetrazole and an acid (solution A);
    (b) providing an aqueous solution of a nitrite salt (solution B);
    (c) heating both solutions to an elevated temperature at or above 65° C.;
    (d) adding solution A to solution B dropwise with rapid stirring and a slow addition rate; and
    (e) cooling the mixture.

7. The method of claim 6, wherein the method comprises reacting about 2 moles to about 5 moles of the nitrite salt per mole of 5-aminotetrazole.

8. The method of claim 7, wherein the method comprises reacting at least 1 mole to about 1.2 moles of the acid per mole of 5-aminotetrazole.

9. The method of claim 6, wherein the nitrite salt is sodium nitrite or potassium nitrite.

10. The method of claim 9, wherein the acid is nitric acid, sulfuric acid, perchloric acid, or hydrochloric acid.

11. The method of claim 10, wherein the method comprises reacting about 2.1 moles of sodium nitrite and about 1.1 mole of nitric acid per mole of 5-aminotetrazole.

12. The method of claim 6, wherein the slow addition rate is a duration that is greater than about 5 minutes.

13. A method for preparing sodium 5-nitrotetrazolate, comprising the steps of:
    (a) providing an aqueous solution of 5-aminotetrazole and nitric acid (Solution A);
    (b) providing an aqueous solution of sodium nitrite (solution B);
    (c) heating both solutions to an elevated temperature at or above 65° C.;
    (d) adding solution A to solution B dropwise with rapid stirring and a slow addition rate; and
    (e) cooling the mixture.

14. The method of claim 13, wherein the method comprises providing about 2.1 moles of sodium nitrite and about 1.1 mole of nitric acid per mole of 5-aminotetrazole.

15. The method of claim 13, wherein the slow addition rate is a duration that is greater than about 5 minutes.

\* \* \* \* \*